United States Patent
Watson et al.

(10) Patent No.: US 9,913,792 B2
(45) Date of Patent: Mar. 13, 2018

(54) METHODS OF REGULATING SKIN HEALTH AND APPEARANCE WITH A COMBINATION OF FLAVONOID AND VITAMIN $B_3$

(71) Applicant: The Procter & Gamble Company, Cincinnati, OH (US)

(72) Inventors: Andrew David Watson, Redhill (GB); Toshihiko Okano, Tokyo (JP); Akira Date, Ashiya (JP)

(73) Assignee: The Procter & Gamble Company, Cincinnati, OH (US)

( * ) Notice: Subject to any disclaimer, the term of this patent is extended or adjusted under 35 U.S.C. 154(b) by 46 days.

(21) Appl. No.: 14/511,445

(22) Filed: Oct. 10, 2014

(65) Prior Publication Data
US 2016/0101031 A1    Apr. 14, 2016

(51) Int. Cl.
*A61K 8/64* (2006.01)
*A61K 8/67* (2006.01)
*A61K 38/17* (2006.01)
*A61K 8/49* (2006.01)
*A61Q 19/08* (2006.01)

(52) U.S. Cl.
CPC ............... *A61K 8/498* (2013.01); *A61K 8/64* (2013.01); *A61K 8/675* (2013.01); *A61K 38/1767* (2013.01); *A61Q 19/08* (2013.01)

(58) Field of Classification Search
CPC ........ A61K 31/455; A61K 8/675; A61K 8/64; A61K 38/00; A61K 38/17
See application file for complete search history.

(56) References Cited

U.S. PATENT DOCUMENTS

| | | |
|---|---|---|
| 5,939,082 A | 8/1999 | Oblong |
| 6,183,761 B1 | 2/2001 | Bissett |
| 2006/0018860 A1* | 1/2006 | Chen ............... A61K 8/498 424/70.14 |
| 2007/0041925 A1* | 2/2007 | Picano ............. A61K 8/0212 424/70.14 |

OTHER PUBLICATIONS

Makrantonaki et al., Molecular Mechanism of Skin Aging—State of the Art, Annals of the New York Academy of Sciences, 2007, pp. 40-50.*

Jacquet et al., Effect of Dietary Supplementation With Inversion® Femme on Slimming, Hair Loss, and Skin and Nail Parameters in Women, Advances in Therapy, 2007, pp. 1155-1171.*

Hughes et al., "Suncreen and Prevention of Skin Aging" Annals of Internal Medicine, 2013, pp. 781-790.*

Niven, "Dolce & Gabbana Launches Skincare", Vogue, Jun. 27, 2014; http://www.vogue.co.uk/beauty/2014/06/27/dolce-and-gabbana-launches-skincare-collection; Accessed on May 10, 2016.*

NvWah;http://www.nywah.com/products/laura_mercier/p_laura_mercier_flawless_skin_tone_perfecting_creme_with_quercetin_plus.html; 2012; Accessed on May 16, 2016.*

Shaoul et al., "Evaluation of the Safety and Efficacy of a Novel Home-Use Device with Diode Arrays and Contact Heating for Facial Skin Rejuvenation", Journal of Cosmetics, Dermatological Sciences and Applications, 2011, pp. 119-124.*

Devi et al., "Evaluation of antioxidant activities of silk protein sericin secreted by silkworm *Antheraea assamensis* (Lepidoptera: Saturniidae)"; Journal of Pharmacy Research 2011,4(12),4688-4691.*

* cited by examiner

*Primary Examiner* — Lianko G Garyu
(74) *Attorney, Agent, or Firm* — John G. Powell; S. Robert Chuey

(57) ABSTRACT

The disclosure relates to topical compositions comprising a flavonoid compound and a vitamin $B_3$ compound, and optionally a hydrolyzed silk protein or fragment thereof, which are useful for improving the health and appearance of aging skin An exemplary composition contains quercetin, hydrolyzed silk sericin and niacinamide.

11 Claims, 10 Drawing Sheets

San Francisco Study

|  | Immediate | | | 2w (N=48) | | | 4w (N=47) | | |
|---|---|---|---|---|---|---|---|---|---|
|  | Cream | NT | p value | Cream | NT | p value | Cream | NT | p value |
| Hydration | 21.47 | 3.52 | <0.001 | 14.69 | 5.42 | <0.001 | 11.07 | -0.24 | <0.001 |
| Cutometer | | | | | | | | | |
| R5 Firm | 0.054 | 0.010 | 0.005 | -0.003 | -0.031 | 0.068 | -0.120 | -0.146 | 0.086 |
| R7 Elastic | 0.018 | 0.004 | 0.045 | 0.017 | -0.008 | 0.007 | -0.053 | -0.072 | 0.031 |
| Spectrophotometer | | | | | | | | | |
| L* | -0.67 | -0.49 | 0.303 | 0.37 | 0.10 | 0.237 | 0.81 | 0.13 | 0.006 |

10A

10B

10C

METHODS OF REGULATING SKIN HEALTH AND APPEARANCE WITH A COMBINATION OF FLAVONOID AND VITAMIN $B_3$

FIELD OF THE INVENTION

The disclosure relates to methods and topical compositions for improving the health and appearance of aging skin.

BACKGROUND OF THE INVENTION

Human skin is comprised of layers. The epidermis is the outermost layer and comprises a cellular continuum of four layers: the stratum corneum, the granular layer, the spinous layer, and the basal layer. Each layer in the epidermis represents various stages along a process in which skin cells undergo a continuous cycle of proliferation, differentiation, and apoptosis.

The basal layer forms the lower portion of the epidermis and contains basal keratinocytes, mitotically active cells that undergo a proliferative cycle to generate daughter cells that are physically dislocated upward into the spinous and granulous layers above. As the cells migrate upward, they lose their central nucleus and start to produce skin proteins (keratins) and fats (lipids). On passing through the spinous and granulous layers, the cells undergo a process of differentiation into corneocytes and undergo morphological changes that flatten their structure as they lose cellular viability, alter their keratin expression profiles, and transform themselves into cellular remnants, thereby forming the stratum corneum. The corneocytes in the stratum corneum remain connected to each other via proteins and lipids, which create a protective barrier against chemical and biological insults from the outside environment. For example, the barrier attenuates the penetration of harmful radiation, including ultraviolet (UV) radiation, into deeper skin layers. The stratum corneum also acts as a permeability barrier and functions to prevent loss of body moisture to the outside environment. Dysfunction of the epidermal barrier can lead to chronic skin conditions, disease, and in extreme cases, can even threaten the viability of the organism.

Skin aging is a multifactorial process driven by both intrinsic and extrinsic factors. Intrinsic factors include chronological aging and other biochemical changes occurring in skin cells. Extrinsic factors include UV exposure, toxins, pollutants, wind, heat, low humidity, harsh surfactants, abrasives, smoke and other environmental elements. On average, a younger epidermis turns over in about one month, shedding the older cells and replacing them with new ones, but the same process can take over forty days in older skin. As skin ages, the cornified layer becomes gradually thinner, which results in a reduction in the functioning capacity of the barrier. Impairment of the barrier allows harmful stimuli to penetrate the stratum corneum more easily, leading to damage of the underlying dermal layers, degradation of the structural proteins collagen and elastin, and eventually skin wrinkling and atrophy. Additionally, the increase in permeability and a reduction in the amount of lipid in the intercellular matrix decreases the capacity of the barrier to diffuse, i.e., remove, toxins from deeper skin layers. The recovery capacity of the barrier to environmental insult is thus substantially reduced with age.

The effects of aging can result in a number of visible changes in the appearance of skin. Thinning of the stratum corneum and general degradation of the skin by intrinsic and/or extrinsic factors increases the visible appearance of fine lines, wrinkles, inflammation, uneven skin tone and other signs of skin aging. For example, in young skin, melanin is evenly distributed, but as skin ages or is exposed to damaging environmental effects, melanocytes lose their normal regulation process and produce excess pigment, leading to areas of hyperpigmentation such as age spots (lentigines) and uneven skin tone.

Topical compositions comprising vitamin $B_3$ compounds are known to effectively regulate skin appearance, as described in U.S. Pat. No. 5,939,082. For example, topical niacinamide can regulate the signs of skin aging, e.g., reduce or efface the visibility of the fine lines, wrinkles, and uneven skin tone associated with aging skin. However, compositions and methods of treatment that are even more effective than currently marketed products at improving the health and appearance of aging skin are continuing desires in the personal care and cosmetic fields.

SUMMARY OF THE INVENTION

The disclosure relates to a method of improving the appearance of aging skin comprising applying an effective amount of a composition comprising flavonols and derivatives or compounds thereof, a vitamin $B_3$ compound, and a dermatologically acceptable carrier. The composition is applied to a skin surface for a period of time sufficient to improve the appearance of at least one sign of aging skin. In some embodiments, the invention relates to a method of improving the appearance of aging skin comprising applying an effective amount of a composition comprising a flavonoid compound, a vitamin $B_3$ compound, a hydrolyzed silk protein or fragment thereof, and a dermatologically acceptable carrier.

The disclosure also relates to a topical composition for improving or preventing the appearance of aging skin comprising a safe and effective amount of a flavonoid compound, a safe and effective amount of a vitamin $B_3$ compound, and a dermatologically acceptable vehicle. In some embodiments, the invention relates to a topical composition for improving or preventing the appearance of aging skin comprising a safe and effective amount of a flavonoid compound, a safe and effective amount of a vitamin $B_3$ compound, a safe and effective amount of a hydrolyzed silk protein or fragment thereof, and a dermatologically acceptable vehicle.

The disclosure also relates to a cosmetic composition comprising a safe and effective amount of a flavonoid compound, a hydrolyzed silk protein, a fragment of a hydrolyzed silk protein, or any combination thereof; a safe and effective amount of a vitamin $B_3$ compound; and a dermatologically acceptable vehicle.

In one aspect, the disclosure provides a method of improving the appearance of aging skin comprising applying an effective amount of a composition comprising: a flavonoid compound, a vitamin $B_3$ compound, and a dermatologically acceptable carrier, to a skin surface, wherein the composition is applied for a period of time sufficient to improve the appearance of at least one sign of aging skin. In some embodiments, the flavonoid compound is obtained from the cocoon of a moth caterpillar, for example, the moth caterpillar *Bombyx mori*, or is extracted from a plant, for example, a plant belonging to the genus *Morus*. In related embodiments, the flavonoid compound is selected from the group consisting of quercetrin, astragalin, quercetin, kaempferol, myricitin, a glycoside of any of the foregoing and any combination thereof, for example, a combination comprising at least two flavonoids. In some embodiments, the vitamin $B_3$ compound is selected from the group consisting of niacinamide, nicotinic acid, nicotinyl alcohol, tocopheryl nicotinate, ethyl nicotinate, methyl nicotinate, and any combination thereof. In related embodiments, the vitamin $B_3$ compound is niacinamide.

In some embodiments, the method comprises applying an effective amount of a composition that further comprises a safe and effective amount of a hydrolyzed silk protein or fragment thereof. In related embodiments, the hydrolyzed silk protein or fragment thereof is obtained from the cocoon of a moth caterpillar, for example, the moth caterpillar *Bombyx mori*. In some embodiments, the hydrolyzed silk protein or fragment thereof is selected from the group consisting of sericin, fibroin, any fragment thereof and any combination thereof. In some embodiments, the hydrolyzed silk protein or fragment thereof is gold silk sericin or silk sericin or a fragment thereof. In related embodiments, the composition comprises from about 0.01 weight percent to about 5 weight percent of the hydrolyzed silk protein or fragment thereof and from about 0.1 weight percent to about 10 weight percent of the vitamin $B_3$ compound. In some embodiments, the composition comprises from about 0.00005 weight percent to about 0.005 weight percent of the flavonoid compound and from about 0.1 weight percent to about 10 weight percent of the vitamin $B_3$ compound. In some embodiments, the ratio by weight of the flavonoid compound to the vitamin $B_3$ compound in the composition is between about 1:10 and about 1:60.

In some embodiments, the method comprises applying an effective amount of the composition to a skin surface, wherein the skin surface is a facial skin surface. In related embodiments, the composition is applied for a period of time sufficient to improve the appearance of at least one sign of aging skin, wherein the sign of aging skin is decreased glycolysis and/or decreased oxidative phosphorylation within a skin cell. In some embodiments, the sign of aging skin is selected from the group consisting of skin inflammation, skin hyperpigmentation, uneven skin tone, skin dryness, skin wrinkling and any combination thereof. In some embodiments, the method comprises applying an effective amount of a composition, wherein the composition is selected from the group consisting of a topical drug composition, a skin care composition, a cosmetic composition and any combination thereof.

In a further aspect, the disclosure provides a topical composition for improving or preventing the appearance of aging skin, comprising: a safe and effective amount of a flavonoid compound; a safe and effective amount of a vitamin $B_3$ compound; and a dermatologically acceptable vehicle. In some embodiments, the flavonoid compound is obtained from the cocoon of a moth caterpillar, for example, the moth caterpillar *Bombyx mori*, or is extracted from a plant, for example, a plant belonging to the genus *Morus*. In related embodiments, the flavonoid compound is selected from the group consisting of quercetrin, astragalin, quercetin, kaempferol, myricitin, a glycoside of any of the foregoing and any combination thereof, for example, a combination comprising at least two flavonoids. In some embodiments, the vitamin $B_3$ compound is selected from the group consisting of niacinamide, nicotinic acid, nicotinyl alcohol, tocopheryl nicotinate, ethyl nicotinate, methyl nicotinate, and any combination thereof. In related embodiments, the vitamin $B_3$ compound is niacinamide.

In some embodiments, the topical composition further comprises a safe and effective amount of a hydrolyzed silk protein or fragment thereof. In related embodiments, the hydrolyzed silk protein or fragment thereof is obtained from the cocoon of a moth caterpillar, for example, the moth caterpillar *Bombyx mori*. In some embodiments, the hydrolyzed silk protein or fragment thereof is selected from the group consisting of sericin, fibroin, any fragment thereof and any combination thereof. In some embodiments, the hydrolyzed silk protein or fragment thereof is gold silk sericin or silk sericin or a fragment thereof. In related embodiments, the topical composition comprises from about 0.01 weight percent to about 5 weight percent of the hydrolyzed silk protein or fragment thereof and from about 0.1 weight percent to about 10 weight percent of the vitamin $B_3$ compound. In some embodiments, the topical composition comprises from about 0.00005 weight percent to about 0.005 weight percent of the flavonoid compound and from about 0.1 weight percent to about 10 weight percent of the vitamin $B_3$ compound. In some embodiments, the ratio by weight of the flavonoid compound to the vitamin $B_3$ compound in the topical composition is between about 1:10 and about 1:60. In related embodiments, the topical composition is selected from the group consisting of a topical drug composition, a skin care composition, a cosmetic composition and any combination thereof.

In another aspect, the disclosure provides a method of preparing a topical composition comprising combining a hydrolyzed silk protein or fragment thereof with a flavonoid compound extracted from the cocoon of a moth caterpillar. In some embodiments, the method further comprises adding a vitamin $B_3$ compound. In a related aspect, the disclosure provides topical compositions comprising a flavonoid compound, a hydrolyzed silk protein or a fragment thereof and a vitamin $B_3$ compound prepared using such methods.

In one aspect, the disclosure provides a method of improving the appearance of aging skin, comprising applying an effective amount of a composition comprising: a flavonoid compound, a vitamin $B_3$ compound, a hydrolyzed silk protein or fragment thereof; and a dermatologically acceptable carrier, to a skin surface, wherein the composition is applied for a period of time sufficient to improve at least one sign of aging skin.

In a further aspect, the disclosure provides topical composition for improving the appearance of aging skin, comprising: a safe and effective amount of a flavonoid compound; a safe and effective amount of a hydrolyzed silk protein or fragment thereof, a safe and effective amount of a vitamin $B_3$ compound; and a dermatologically acceptable vehicle.

In one aspect, the disclosure provides a cosmetic composition comprising: a safe and effective amount of a flavonoid compound, a hydrolyzed silk protein, a fragment of a hydrolyzed silk protein, or any combination thereof; a safe and effective amount of a vitamin B3 compound; and a dermatologically acceptable vehicle.

Other features and advantages of the present disclosure will become apparent from the following detailed description, including the drawings. It should be understood, however, that the detailed description and the specific examples, while indicating preferred embodiments, are provided for illustration only, because various changes and modifications within the spirit and scope of the invention will become apparent to those skilled in the art from the detailed description.

BRIEF DESCRIPTION OF THE DRAWINGS

While the specification concludes with claims particularly pointing out and distinctly claiming the subject matter that is regarded as the disclosure, it is believed that the invention will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

FIG. 2A shows the ECAR at time point 13 following treatment. FIG. 2B shows the ECAR at time point 20 following treatment.

FIG. 4A shows cells treated with 0.05% Croda Crosilk™ 10000. FIG. 4B shows cells treated with 0.05% Croda Crosilk™ Liquid.

FIG. 8A shows inhibition of melanin production in B16 mouse melanoma cells treated with various concentrations of gold silk sericin. FIG. 8B shows the inhibition stem cell factor (SCF) release from human keratinocytes treated with various concentrations of gold silk sericin.

FIG. 9 shows skin assessment measurements following treatment with a composition comprising gold silk sericin and niacinamide for 0, 2, and 4 weeks in a clinical study.

FIG. 10A shows skin at baseline (pre-treatment). FIG. 10B shows skin after treatment with a skin cream comprising gold silk sericin, niacinamide, and olive oil in a dermatologically acceptable vehicle. FIG. 10C shows skin after treatment with the vehicle only for eight weeks.

DETAILED DESCRIPTION OF THE INVENTION

Figure 1:
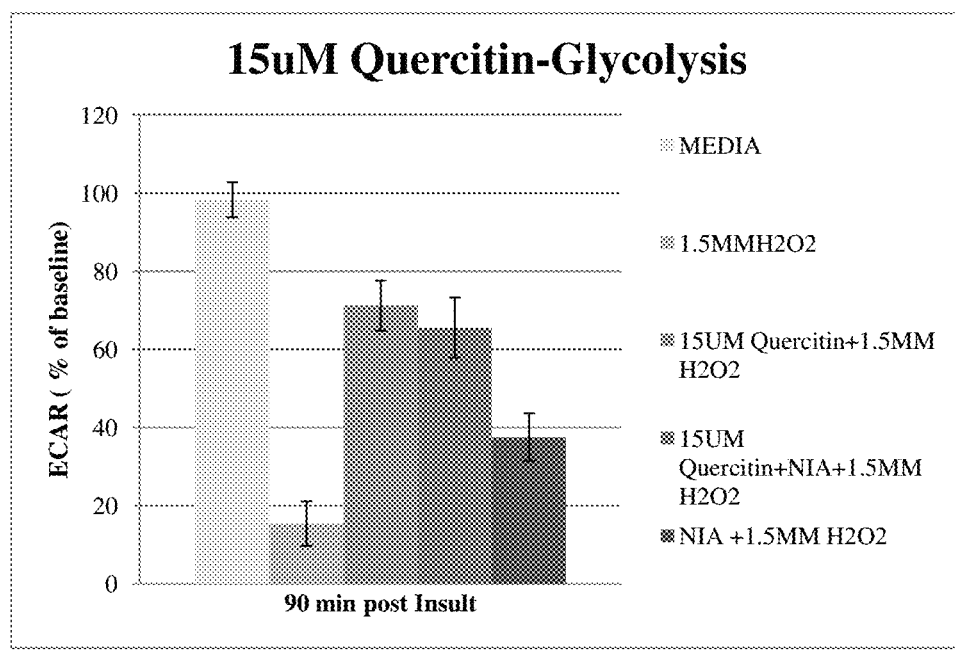
FIG. 1 shows the extracellular acidification rate (ECAR) as a percentage of baseline in human fibroblasts treated with 1.5 mM hydrogen peroxide and 15 uM quercetin and/or 3% niacinamide at 90 minutes following treatment.

The disclosure provides topical compositions comprising a flavonoid compound and a vitamin $B_3$ compound, and optionally a hydrolyzed silk protein or fragment thereof, and methods of using such compositions that provide previously unrecognized benefits in regulating skin condition. Various aspects of the disclosure provide topical compositions for prophylactically and/or therapeutically improving the appearance of aging skin, comprising a combination of a flavonoid compound and a vitamin $B_3$ compound, and optionally a hydrolyzed silk protein or fragment thereof. The disclosure also relates to methods of providing such regulation and/or improvement using the subject compositions.

In one aspect, the combination of a flavonoid compound and a vitamin $B_3$ compound, and optionally a hydrolyzed silk protein or fragment thereof, protects the skin from stressors that contribute to aging skin. Examples of stressors include, but are not limited to, environmental factors such as heat, pollutants, and UV radiation, which can exacerbate the generation of reactive oxygen species (ROS). ROS are molecules formed within cells as a by-product of oxygen metabolism that can damage cellular structures and organelles such as mitochondria. Although cells can defend against ROS by using redox regulators such as glutathione and NAD, as well as various enzymes that neutralize ROS, such defenses can be overwhelmed by a stressor-induced surge in ROS, leading to acute and potentially chronic alterations in energy homeostasis and metabolism that can cause cellular dysfunction.

In one aspect, the combination of a flavonoid compound and a vitamin $B_3$ compound and optionally a hydrolyzed silk protein or fragment thereof synergistically increases cellular energy production. One sign of aging skin is a reduction in the ability of skin cells to produce energy in the form of adenosine trisphosphate (ATP). Cells require adequate energy to defend against stressors and prevent damage. Two key metabolic pathways for mammalian cells to produce energy are the glycolytic pathway and the oxidative phosphorylation pathway, and the energy-making processes of cells can be assessed using metabolic indicators associated with these pathways. The identification and use of such metabolic indicators to identify synergistic combinations of skin care actives is described in U.S. Patent Application No. 61/711,521, incorporated herein by reference.

Glycolysis is the metabolic pathway that converts glucose into pyruvate. The free energy released in this process is used to form ATP. A by-product of glycolysis is lactic acid, which can form a lactate anion and a proton in solution. Lactic acid, lactate, or proton concentration can be used as a metabolic indicator of glycolysis, so a change in extracellular pH or extracellular acidification rate may be directly correlated to energy production by the cell via the glycolytic pathway. A higher extracellular acidification rate may indicate an increase in energy produced via the glycolysis pathway, and thus an improvement in the metabolism and/or health of a cell. Conversely, a lower extracellular acidification rate may indicate a decrease in glycolysis.

Oxidative phosphorylation involves the transfer of electrons from electron donors to electron acceptors and uses oxygen to generate ATP. The rate at which a cell consumes oxygen may be directly correlated to energy production by the cell via the oxidative phosphorylation pathway. A higher oxygen consumption rate or carbon dioxide production rate may indicate an increase in energy produced via the oxidative phosphorylation pathway, and thus an improvement in the metabolism and/or health of the cell. Conversely, a lower oxygen consumption rate or carbon dioxide production rate may indicate a decrease in oxidative phosphorylation.

In one aspect, the compositions and methods of the disclosure are useful for reducing skin inflammation.

In another aspect, the compositions and methods of the disclosure are useful for reducing the appearance of skin hyperpigmentation. For example, the compositions and methods of the disclosure are useful for skin lightening. Skin lightening involves diminishing, minimizing, and/or effacing existing melanin in skin (therapeutic), and/or delaying, minimizing and/or preventing the formation of melanin in skin (prophylactic).

All percentages and ratios used herein are by weight of the total composition, and all measurements made are at 25° C. unless otherwise designated. All numeric ranges are inclusive of narrower ranges; delineated upper and lower range limits are interchangeable to create further ranges not explicitly delineated. All statistical analyses are performed such that a p-value of less than 0.5 indicates statistical significance.

The compositions and methods of the disclosure can comprise, consist essentially of, or consist of, the essential components, as well as optional ingredients described herein.

The terms "apply" or "application," as used herein in reference to a composition refers to contacting a mammalian skin surface, such as the epidermis, with a topical composition.

The term "dermatologically acceptable" as used herein refers to a component that may be used in contact with mammalian skin tissue without undue toxicity, incompatibility, instability, allergic response, and the like. The term "dermatologically acceptable carrier" as used herein refers to a carrier that is suitable for topical application to keratinous tissue, has acceptable aesthetic properties, is compatible with the active compounds, and does not cause any safety or toxicity concerns.

The term "cosmetic" as used herein refers to providing a desired visual effect on an area of a mammalian body. The visual effect may be temporary, semi-permanent, or permanent.

Some non-limiting examples of "cosmetic products" include products that alter the appearance of facial and/or body skin or facial features, including foundations, eye liners, eye shadows, blushes, bronzers, highlighters, lip liners, brow pencils, blemish/beauty balm (BB) creams, color correcting/control (CC) creams, lipsticks, mascaras, lip glosses, lip balms, concealers, and powders.

The terms "safe and effective" or "effective amount" as used herein refers to an amount of a compound or composition sufficient to induce a positive benefit without serious side effects (i.e., to provide a reasonable benefit-to-risk ratio, within the scope of sound judgment of the skilled artisan).

The terms "age spot" or "hyperpigmentation" as used herein refer to a defined area of skin wherein the pigmentation is greater than that of an adjacent area due to the localized and chronic overproduction of melanin caused by intrinsic or extrinsic aging factors. Hyperpigmentation can include one or more of sun spots, liver spots, blotchiness, mottling, chloasma, solar lentigos, hypo-melanotic lesions, freckles, and melasma spots.

The term "facial skin surfaces" as used herein refers to one or more of forehead, periorbital, cheek, perioral, chin, and nose skin surfaces.

The term "stressor" as used herein refers to an environmental element that alters cellular physiology, for example, by causing the formation of ROS. Non-limiting examples of stressors include UV radiation, cigarette smoke, ozone, engine exhaust, smog, surfactants, and radiation from electronics.

The term "skin care composition" as used herein refers to a composition suitable for topical application to mammalian skin. Non-limiting example of skin care compositions include cleansers (e.g., liquid, bar, oil, or foam), toners, serums, masks, lotions, creams, ointments, balms, oils, scrubs, and treatments. Skin care compositions regulate and/or improve various skin conditions. For example, a skin care composition can provide one or more of the following effects: improve skin appearance and/or feel by providing a smoother, more even appearance and/or feel; increase the thickness of one or more layers of the skin; improve the elasticity or resiliency of the skin, improve the firmness of the skin; reduce the oily, shiny, or dull appearance of skin; improve the hydration status or moisturization of skin; minimize the appearance of fine lines or wrinkles; improve skin exfoliation or desquamation; plump the skin; soften the skin; improve skin barrier properties; improve skin tone; reduce the appearance of inflammation, redness or skin blotches or hyperpigmentation; and improve the brightness, radiance, or translucency of skin.

The term "diluent" as used herein refers to a material in which the flavonoid compound and vitamin $B_3$ compound, and optionally a hydrolyzed silk protein or fragment thereof, can be dispersed, dissolved, or otherwise incorporated.

The terms "synergy," "synergistic" and "synergistically" as used herein refer to a combination of two or more active agents wherein the combination provides an advantage (e.g., biological, economic, and/or regulatory) over using each active alone. The terms can also refer to a combination that provides an advantage over the expected effect of the combination. For example if a combination of two or more actives is expected to have an additive effect, meaning the effect provided by the combination of actives is expected to be equal to or substantially equal to the sum of the individual effects of the actives, then the combination is synergistic if it provides a more than additive effect. In some embodiments, synergy may be demonstrated by a combination of actives acting on different metabolic pathways (e.g., glycolysis and oxidative phosphorylation) to improve the appearance of aging skin more than either active alone. In some embodiments, synergy may be demonstrated by a combination of actives that each act on a difference type of cell (e.g., keratinocytes and melanocytes) to improve the appearance of aging skin. In some embodiments, synergy may be demonstrated by a combination of actives that do not inhibit one another with respect to improving the appearance of aging skin. In some embodiments, synergy may be demonstrated by a combination of actives wherein one or more actives provides a metabolic benefit and one or more actives provides a non-metabolic benefit (e.g., economic, formulation, regulatory, and/or safety), to improve the appearance of aging skin.

The term "improving the appearance of aging skin" as used herein refers to effecting a visually and/or tactilely perceptible positive change or benefit in skin appearance and/or feel. As used herein, "improving the appearance of aging skin" also refers to preventing or delaying the appearance of aging skin. A perceptible positive change or benefit can include, for example, a change in the size, length, number, diameter, width, volume, degree, grade, depth, color, height and/or surface area of a sign of aging skin. Benefits that may be provided by the disclosure include, but are not limited to, one of more of the following: reducing the appearance of wrinkles and coarse deep lines, inflammation, fine lines, crevices, bumps, blemishes and/or large pores; thickening of keratinous tissue; increasing the convolution of the dermal-epidermal border (also known as the rete ridges); increasing the collagen and/or elastin content of the skin; lightening the skin; preventing loss of skin elasticity, for example, due to loss, damage and/or inactivation of functional skin elastin resulting in such conditions as elastosis, sagging, and loss of skin recoil; improving the coloration of the skin, for example, reducing under-eye circles, blotchiness (e.g., uneven red coloration due to, for example, rosacea), sallowness, and hyperpigmentation; and increasing moisture content.

The term "signs of aging skin" as used herein, includes, but is not limited to, all visibly and tactilely perceptible manifestations, as well as any macro- or micro-effects, of aging skin. The signs may result from processes which include, but are not limited to, the development of textural discontinuities such as wrinkles, fine lines, skin lines, crevices, bumps, blemishes, large pores, uneven skin tone or roughness; discoloration (including undereye circles); blotchiness; scaliness, flakiness, inflammation, puffiness, dryness; sallowness; dullness; hyperpigmented skin regions such as age spots and freckles; inflammation; keratoses; abnormal differentiation; hyperkeratinization; elastosis; collagen breakdown; and other histological changes in the stratum corneum, dermis, epidermis, vascular system (e.g., telangectasia or spider blood vessels), and underlying tissues (e.g., fat and/or muscle), especially those proximate to the skin. Additionally, the disclosure is not to be limited to regulation of the above mentioned "signs of aging skin" which arise due to mechanisms associated with aging, but is intended to include regulation of said signs irrespective of the mechanism(s) of origin.

The term "regulating skin condition" as used herein refers to prophylactically and/or therapeutically affecting skin condition, including improving visible and/or tactile changes in skin. The term "prophylactically regulating skin condition" as used herein includes delaying, minimizing and/or preventing visible and/or tactile signs of aging skin. The term "therapeutically regulating skin condition" as used herein includes ameliorating, diminishing, minimizing, and/or effacing signs of skin aging. The term "regulating skin condition" is intended to include regulation of signs of skin aging irrespective of the mechanism(s) of origin of said signs.

I. Compositions

Embodiments of the disclosure comprise a combination of a flavonoid compound and a vitamin $B_3$ compound and optionally a hydrolyzed silk protein or fragment thereof and a dermatologically acceptable carrier. The compositions according to the invention improve the appearance of aging skin to a degree that is unexpectedly advantageous or superior compared to the compounds individually.

Compositions of the disclosure may be made into a wide variety of product forms that include, but are not limited to, solutions, suspensions, emulsions, lotions, creams, gels, ointments, balms, toners, sticks, pencils, sprays, aerosols, ointments, pastes, foams, powders, mousses, wipes, strips, patches, and masks. The foregoing product forms may be provided to a consumer as a skin care product for the face and/or body, including, but not limited to, cleansers (e.g., liquid, bar, oil, or foam), toners, serums, masks, lotions, creams, ointments, balms, oils, scrubs, and treatments. Embodiments of the disclosure may also be provided as a cosmetic product, including, but not limited to, foundations, eye liners, eye shadows, blushes, bronzers, highlighters, lip liners, brow pencils, blemish/beauty balm (BB) creams, color correcting/control (CC) creams, lipsticks, mascaras, lip glosses, lip balms, concealers, and powders. The composition form may follow from the particular dermatologically acceptable carrier chosen.

In some embodiments, the compositions of the disclosure are formulated to have a pH of 10.5 or below. The pH values of some embodiments range from about 2 to about 10.5, or from about 3 to about 8, or from about 4 to about 7.

In some embodiments, the composition are provided in a package sized to store a sufficient amount of the composition for the treatment period. The size, shape, and design of the packages may vary widely and are known in the art.

A. Flavonoid Compound

The compositions of the disclosure comprise a safe and effective amount of one or more flavonoid compounds. Flavonoid compounds are plant pigments that have been shown to have anti-inflammatory, anti-microbial, anti-cancer, and antioxidant properties. A suitable flavonoid compound may comprise a compound from any class of flavonoids, for example, bioflavonoids (containing a 2-phenyl-1,4-benzopyrone backbone), isoflavonoids (containing a 3-phenyl-1,4-benzopyrone structure) and neoflavonoids (containing a 4-phenyl-1,2-benzopyrone structure). Similarly, a suitable flavonoid compound may comprise a compound from any subclass of flavonoids, e.g., anthocyanidins, flavanols, flavanones, flavonols, flavones, and isoflavones. In some embodiments, the flavonoid compound comprises a flavanol, i.e., a flavonoid compound having a 3-hydroxy-2-phenylchromen-4-one backbone.

Flavonoid compounds can be obtained from naturally occurring sources using extraction methods known in the art and also are commercially available (e.g., from Tocris Bioscience, England). In some embodiments, the flavonoid compound is obtained from a plant, for example, a tree, bush, flower, grass, or herb. The flavonoid compound can be obtained from any part of a plant, e.g., the stem, root, leaf, bud, bark, seed, flower, petal, and/or fruit. In some embodiments, the flavonoid compound is obtained from the leaf of a plant, for example, from the leaf of a plant belonging to the genus *Morus*, as exemplified by the mulberry tree. Mulberry leaves contain two major flavonol glycosides, quercetrin and astragalin. In another embodiment, the flavonoid compound is obtained from the cocoon of a moth caterpillar, for example, from the cocoon of the silkworm *Bombyx mori*, a moth caterpillar that eats mulberry leaves. The cocoon shell of *Bombyx mori* contains two major flavonol glycosides, quercetrin and astragalin, and two minor flavonol aglycones, quercetin and kaempferol. In another embodiment, the flavonoid compound is chemically synthesized using conventional methods known in the art.

In another embodiment, the flavonoid compound is a flavonol selected from the group consisting of quercetrin, astraglin, quercetin, kaempferol, myricitin, a glycoside of any of the foregoing, and any combination thereof. In some embodiments, the flavonoid compound comprises a combination of at least two flavonols, for example, a combination of two, three, four, or five flavonols. In some embodiments, the flavonoid compound comprises quercetin (2-(3,4-dihydroxyphenyl)-3,5,7-trihydroxy-4H-chromen-4-one). Quercetin is a flavonol compound known for having anti-histamine and anti-oxidant properties and can significantly increase the rate of glycolysis in stressed cells (FIG. 1).

In the compositions of the disclosure, the flavonoid compound may comprise greater than about 0.00001 weight percent of the composition. In the compositions of the disclosure, the flavonoid compound may comprise from about 0.00001 weight percent to about 0.5 weight percent, more preferably from about 0.00005 weight percent to about 0.005 weight percent of the composition.

B. Vitamin $B_3$ Compound

In addition to a flavonoid compound, the compositions of the disclosure comprise a safe and effective amount of one or more vitamin $B_3$ compounds. A suitable vitamin $B_3$ compound is a precursor of nicotinamide adenine dinucleotide (NAD) and/or a precursor of nicotinamide adenine dinucleotide phosphate (NADP). Examples of suitable vitamin $B_3$ compounds are described in U.S. Pat. No. 5,939,082, incorporated herein by reference, and include, but are not limited to, niacinamide, nicotinic acid, nicotinyl alcohol, tocopheryl nicotinate, ethyl nicotinate, methyl nicotinate, and derivatives and/or salts of any of the foregoing. In some embodiments, the vitamin $B_3$ compound is niacinamide.

Suitable vitamin $B_3$ compounds are commercially available (e.g., from Sigma-Aldrich, St. Louis, Mo.). In the compositions of the disclosure, the vitamin $B_3$ compound may comprise from about 0.01 weight percent to about 50 weight percent, or from about 0.1 weight percent to about 10 weight percent, or from about 1 weight percent to about 5 weight percent of the composition.

In some embodiments, the composition comprises from about 0.00005 weight percent to about 0.005 weight percent of the flavonoid compound and from about 0.1 to about 10 weight percent of the vitamin $B_3$ compound. In some embodiments, the ratio of the flavonoid compound to the vitamin $B_3$ compound in the composition is between about 1:10 and about 1:60.

C. Hydrolyzed Silk

The compositions of the disclosure may further comprise a safe and effective amount of one or more hydrolyzed silk proteins or fragments thereof. In some embodiments, the hydrolyzed silk protein is obtained from the cocoon of a moth caterpillar, for example, from the cocoon of the silkworm *Bombyx mori*. In some embodiments, the hydrolyzed silk protein is selected from the group consisting of sericin, fibroin, any fragments thereof and any combination thereof.

A hydrolyzed silk protein or fragment thereof can be obtained from silk fibers using extraction methods known in the art and are also commercially available (e.g., from Croda International, PLC, England).

In some embodiments, a composition of the disclosure includes a combination of hydrolyzed silk sericin and flavonoids known as "gold silk sericin" (GSS) One example of GSS is Golden Flavo-Silk™ (BioSpectrum, Republic of Korea). GSS may be obtained by combining hydrolyzed silk sericin and flavonoid compounds isolated from the cocoon shell of the silkworm *Bombyx mori* under conditions that preserve the bioactivity of the flavonoid compounds. GSS may also be obtained by combining hydrolyzed silk sericin with a flavonoid compound obtained from another source In the compositions of the disclosure, the hydrolyzed silk protein or fragment thereof may comprise greater than about 0.001 weight percent of the composition. In the compositions of the disclosure, the hydrolyzed silk protein or fragment thereof may comprise from about 0.002 weight percent to about 5 weight percent, or from about 0.005 weight percent to about 1 weight percent, or from about 0.01 weight percent to about 5 weight percent of the composition. In some embodiments, the composition comprises from about 0.01 weight percent to about 5 weight percent of the hydrolyzed silk protein or fragment thereof and from about 0.1 weight percent to about 10 weight percent of the vitamin $B_3$ compound.

D. Dermatologically Acceptable Carrier

The compositions of the disclosure comprise a dermatologically acceptable carrier. Concentrations of the dermatologically acceptable carrier can vary with the carrier selected and the intended concentrations of the essential and optional components of the composition. In various embodiments, the carrier is present at a level from about 50 weight percent to about 99 weight percent, about 60 weight percent to about 98 weight percent, about 70 weight percent to about 97 weight percent, or from about 80 weight percent to about 95 weight percent, of the composition.

The combination of a flavonoid compound and a vitamin $B_3$ compound, and optionally a hydrolyzed silk protein or fragment thereof, is incorporated into the dermatologically acceptable carrier to enable the active compounds to be delivered to the skin at appropriate concentrations. The dermatologically acceptable carrier can thus act as a diluent, dispersant, solvent, or the like for the active compounds to ensure that they can be applied to, and distributed evenly over, the selected target. The dermatologically acceptable carrier may contain one or more dermatologically acceptable solid, semi-solid, or liquid fillers, diluents, solvents, extenders, and the like. The dermatologically acceptable carrier can be inert or can itself possess dermatological benefits of its own. Suitable dermatologically acceptable carriers include conventional or otherwise known carriers. The dermatologically acceptable carrier is physically and chemically compatible with the essential components described herein and should not unduly impair stability, efficacy or other benefits associated with the compositions of the disclosure.

The dermatologically acceptable carrier can be provided in a wide variety of solid, semi-solid, or liquid forms. Non-limiting examples include simple solutions (aqueous or oil-based), emulsions, and solid forms (gels, sticks, flowable solids, amorphous materials).

In certain embodiments, the dermatologically acceptable carrier comprises a hydrophilic diluent. Examples of hydrophilic diluents include, but are not limited to, water, inorganic hydrophilic diluents such as lower monovalent alcohols (e.g., having one to four carbon atoms) and lower molecular weight glycols and polyols, including propylene glycol, polyethylene glycol, polypropylene glycol, glycerol, butylene glycol, 1,2,4-butanetriol, sorbitol esters, 1,2,6-hexanetriol, ethanol, isopropanol, sorbitol esters, butanediol, ether propanol, ethoxylated ethers, propoxylated ethers and combinations thereof.

In certain embodiments, the dermatologically acceptable carrier is in the form of an emulsion. An emulsion may be generally classified as having a continuous aqueous phase (e.g., oil-in-water or water-in-oil-in-water) or a continuous oil or silicone phase (e.g., water-in-oil, oil-in-water-in-oil, or water-in-silicone). The oil phase may comprise silicone oils or non-silicone oils such as hydrocarbon oils, esters, ethers, and mixtures thereof.

The aqueous phase typically comprises water. In other embodiments, the aqueous phase may comprise non-water components, including, but not limited to, water-soluble moisturizing agents, conditioning agents, anti-microbials, humectants and/or other water-soluble skin care agents. In some embodiments, the non-water component of the composition comprises a humectant such as glycerin and/or other polyols.

Emulsions may further comprise an emulsifier. A composition may comprise any suitable percentage of emulsifier to sufficiently emulsify the composition. Suitable weight ranges include from about 0.1% to about 10% or about 0.2% to about 5% of an emulsifier, based on the weight of the composition. Emulsifiers may be nonionic, anionic or cationic. Suitable emulsifiers are disclosed in, for example, McCutcheon's Detergents and Emulsifiers: North American Edition, pages 317-324 (1986), incorporated herein by reference. Suitable emulsions may have a wide range of viscosities, depending on the desired product form. The carrier may further comprise one or more thickening agents known in the art to provide compositions having a suitable viscosity and rheological character.

E. Optional Agents

The compositions of the disclosure may optionally comprise one or more of the following agents: anti-inflammatory agents, sunscreens or sunblocks, anti-acne agents, retinoids, emollients, moisturizers, desquamation agents, humectants, exfoliants, anti-cellulite agents, chelating agents, self-tanning agents, non-vitamin antioxidants and radical scavengers, hair growth regulators, anti-wrinkle agents, skin-lightening agents, anti-atrophy agents, minerals, phytosterols and/or plant hormones, N-acyl amino acid compounds, anti-microbial or anti-fungal agents, plant serums, and other useful skin care and cosmetic agents known in the art.

The compositions of the disclosure may also comprise one or more of a wide variety of cosmetic and pharmaceutical ingredients commonly used in skin care and cosmetic products, for example, as described in the Personal Care Product Council's International Cosmetic Ingredient Dictionary and Handbook, $14^{th}$ Edition (2012), incorporated herein by reference. Examples of such ingredients include, but are not limited to, abrasives, absorbents, acids, aesthetic components (e.g., fragrances, pigments, dyes), essential oils, anti-caking agents, anti-foaming agents, anti-microbials, binders, biological additives, buffering agents, bulking agents, chemical additives, astringents, biocides, denaturants, emollients, analgesics, natural extracts, film formers or materials, oils, opacifying agents, polymers, pH adjusters, preservatives, propellants, reducing agents, sequestrants, skin cooling agents, skin protectants, stabilizers, surfactants, thickeners, viscosity modifiers, vitamins, waxes, and combinations thereof.

II. Exemplary Compositions

The following are non-limiting examples of the compositions of the disclosure. The examples are given solely for the purpose of illustration and are not to be construed as limitations of the disclosed subject matter. One of ordinary skill in the art would recognize that many variations are possible that do not depart from the spirit and scope of the invention. In the examples, all concentrations are listed as weight percent, unless otherwise specified, and may exclude minor materials such as diluents, solvents, fillers, and so forth. The listed formulations, therefore, comprise the listed components and any minor materials associated with such components. As is apparent to one of ordinary skill in the art, the selection of these minor materials will vary depending on the physical and chemical characteristics of the particular ingredients selected to make the disclosure as described herein.

Examples of some compositions are provided below.

| Component | Ex. A | Ex. B | Ex. C |
|---|---|---|---|
| | Weight Percent | | |
| Flavonoid(s) (e.g., quercetin) | 0.00005 to 0.005 | | |
| Vitamin $B_3$ (e.g., niacinamide) | 0.1 to 10 | | |
| Hydrolyzed Silk (optional) | 0.01 to 5 | | |
| Isohexadecane | 3.00 | 0 | 0 |
| Acryl amide/Sodium Acryloydimethyltaurate Copolymer | 1.00 | 0 | 0 |
| Dimethicone | 1.00 | 0 | 0 |
| Glycerin | 2.00 | 1.00 | 10.00 |
| Isopropyl Isostearate | 1.33 | 0 | 0 |
| Propylene Glycol | 1.00 | 0 | 0 |
| Panthenol | 0.05 | 0 | 0.50 |
| Stearyl Alcohol | 1.00 | 1.00 | 0 |
| Cetyl Alcohol | 0.50 | 1.00 | 0 |
| Benzyl Alcohol | 0.50 | 0 | 0 |
| Phenoxyethanol | 0.25 | 0.50 | 0.25 |

-continued

| Component | Ex. A | Ex. B | Ex. C |
|---|---|---|---|
| | Weight Percent | | |
| Cetearyl Glucoside | 0.10 | 0 | 0 |
| Ethyl paraben | 0.05 | 0 | 0 |
| Stearic Acid | 0.10 | 0.10 | 0 |
| PEG-100 Stearate | 0.10 | 0 | 0 |
| Propylparaben | 0.10 | 0.10 | 0.25 |
| Methylparaben | 0.10 | 0.20 | 0 |
| PEG-4 Laurate | 0.06 | 0 | 0 |
| Tocopherol | 0.05 | 0 | 0 |
| Disodium EDTA | 0.05 | 0.10 | 0 |
| Fragrance | 0.00 | 0.10 | 0 |
| Petrolatum, USP | 0 | 1.00 | 0 |
| Mineral Oil | 0 | 8.00 | 0 |
| Steareth-21 Polyoxyethylene Stearyl Ether | 0 | 0.50 | 0 |
| Decyl Glucoside | 0 | 0.50 | 0 |
| Steareth-2 | 0 | 0.25 | 0 |
| Carbomer 954 | 0 | 0.16 | 0 |
| Acrylates C10-30 Alkyl Acrylate Crosspolymer | 0 | 0.12 | 0 |
| Tocopheryl Acetate | 0 | 0.10 | 0.50 |
| Sodium Hydroxide | 0 | 0.05 | 0 |
| Cyclomethicone | 0 | 0 | 78.56 |
| PEG/PPG-18/18 Dimethicone | 0 | 0 | 2.00 |
| Iron Oxides (red, black, yellow) | 0 | 0 | 1.50 |
| Titanium Dioxide | 0 | 0 | 8.34 |
| Talc | 0 | 0 | 3.00 |
| Paraffin | 0 | 0 | 0.50 |
| Arachidyl Behenate | 0 | 0 | 0.30 |
| Trihydroxystearin | 0 | 0 | 0.30 |
| Laureth-7 | 0 | 0 | 0.50 |
| Nylon-12 | 0 | 0 | 0.60 |
| Sodium Chloride | 0 | 0 | 2.00 |
| Sodium Dehydroacetate | 0 | 0 | 0.30 |
| Niacinamide | 0 | 0 | 2.00 |
| Trisodium EDTA | 0 | 0 | 0.10 |
| Water | QS | QS | QS |
| Total Weight | 100 | 100 | 100 |

The compositions of the disclosure are generally prepared by conventional methods known in the art. Such methods typically involve mixing of the ingredients in one or more steps to a relatively uniform state, optionally with heating, cooling, application of vacuum, and the like. Typically, emulsions are prepared by first mixing the aqueous phase materials separately from the oil phase materials and then combining the two phases as appropriate to yield the desired continuous phase. The compositions are preferably prepared so as to optimize stability (physical stability, chemical stability, photostability) and/or delivery of the active materials. The optimization may include appropriate pH (e.g., less than 7), exclusion of materials that can complex with the active agent(s) and thus negatively impact stability or delivery (e.g., exclusion of contaminating iron), use of approaches to prevent complex formation (e.g., appropriate dispersing agents or dual compartment packaging), use of appropriate photostability approaches (e.g., incorporation of sunscreen/sunblock, use of opaque packaging), and the like, as would be known in the art.

III. Methods of Treatment

The compounds described herein may be used in various methods of treatment. In some embodiments, the method of improving the appearance of aging skin comprises applying a composition to the skin surface, wherein the composition is applied for a period of time sufficient to improve the appearance of aging skin.

Skin surfaces of the most concern tend to be those typically exposed to the environment, such as facial skin surfaces, hand and arm skin surfaces, foot and leg skin surfaces, and neck and chest skin surfaces (e.g., décolletage). In some embodiments, compositions of the disclosure are applied to facial skin surfaces, such as the forehead, perioral region, chin, periorbital region, nose, and/or cheek skin surfaces. In some embodiments, improving the appearance of aging skin comprises improving or preventing the appearance of wrinkles, fine lines, coarse deep lines, crevices, bumps, large pores, inflammation, hyperpigmentation, age spots, skin dryness, loss of skin elasticity, skin sagging, loss of skin recoil, loss of skin firmness, blotchiness, sallowness, blemishes and combinations thereof.

The method comprises the step of applying the composition to the skin surface. Many regimens exist for the application of the composition. In some embodiments, the composition is chronically applied to the skin. The composition may be applied at least once a day, twice a day, or on a more frequent daily basis, during a treatment period. The treatment period may vary. In some embodiments, the treatment period is between about one week and about twelve weeks. In some embodiments, the treatment period is between about four weeks and about twelve weeks. In some embodiments, the treatment period is between about four weeks and about eight weeks. In some embodiments, the treatment period will extend over multiple months (e.g., about three to about twelve months) or multiple years.

In some embodiments, the composition is applied once a day during the treatment period, for example, before sleeping. In some embodiments, the composition is applied twice a day during the treatment period. When applied twice daily, the first and second applications may be separated by about one to about sixteen hours. For example, the composition may be applied in the morning after waking and in the evening before sleeping. In some embodiments, the composition is applied and massaged into the skin. The composition can also be applied so that it remains visible on the surface of the skin, e.g., for a cosmetic composition. The composition may be applied broadly, e.g., to one or more skin surfaces, or the application may be localized such that the composition is delivered to a targeted area while minimizing delivery to other skin surfaces. For example, the composition may be applied to a discrete area, such as an age spot, or to a specific facial region, such as the cheek.

A wide range of quantities of the compositions of the disclosure can be employed to improve at least one sign of aging skin. In some embodiments, the quantity applied, in milligrams of composition per square centimeter of skin, is from about 0.1 mg/cm$^2$ to about 10 mg/cm$^2$. In some embodiments, the method comprises applying a composition in the form of a skin lotion, skin cream, or cosmetic product, that is intended to be left on the skin for some esthetic, prophylactic, therapeutic or other benefit (i.e., a "leave-on" composition). After applying the composition to a skin surface, the composition is may be left on the skin for a period of at least about 15 minutes, or at least about 30 minutes, or at least about one hour.

In some embodiments, the composition may be delivered by a variety of applicators appropriate for general and/or localized application. Examples of such applicators include, but are not limited to, droppers, wands, swabs, brushes, sponges, pads, balls, puffs, pens or any other suitable device. In some embodiments, the composition is applied directly using one's finger or in other conventional manners known in the art.

The treatment period and/or application frequency should be sufficient to provide an improvement in at least one sign of aging skin.

Example 1

Figure 2:
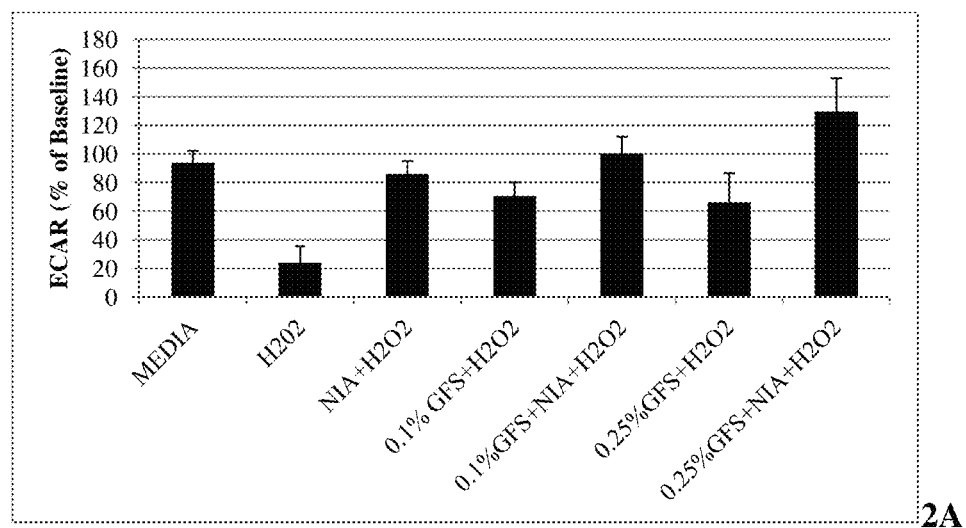
FIG. 2 shows the ECAR as a percentage of baseline in human fibroblasts treated with 1.75 mM hydrogen peroxide and 3% niacinamide and/or 0.1% or 0.25% gold silk sericin.
Figure 2:
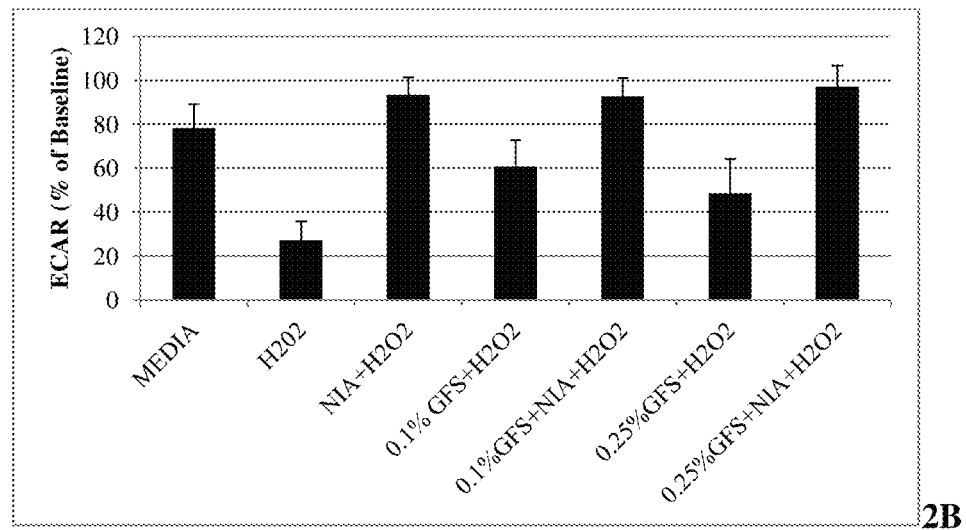

The effect of a combination of a flavonoid compound, a vitamin B$_3$ compound, and a hydrolyzed silk protein on cellular energy production was assessed by measuring the extracellular acidification rate ("ECAR") of fibroblasts after exposure to hydrogen peroxide challenge (FIG. 2). ECAR provides an indirect measure of glycolysis. Treatment with hydrogen peroxide replicates stress induced by UV radiation or chemical pollution and decreases the ECAR. An XF Extracellular Flux Analyzer (Seahorse Bioscience, North Billerica, Mass.) was used to detect extracellular acidification rate. Human dermal fibroblasts were plated at 1×10$^5$ cells per well in a 96-well plate 24 hours prior to testing. The plate was loaded into the analyzer and equilibrated according to the manufacturer's instructions. Hydrogen peroxide, quercetin (Tocris Bioscience), GSS (BioSpectrum) and niacinamide were loaded into an automated injection port of the XF cartridge plate. The analyzer was programmed to sequentially run a two-minute mix cycle and a four-minute measurement cycle continuously for at least 108 minutes. Data points were collected and recorded by the analyzer. The analyzer was allowed to complete three cycles to establish a baseline value for glycolysis prior to being exposed to the peroxide solution. Each test condition used 8 wells of the 96-well plate.

Figure 3:
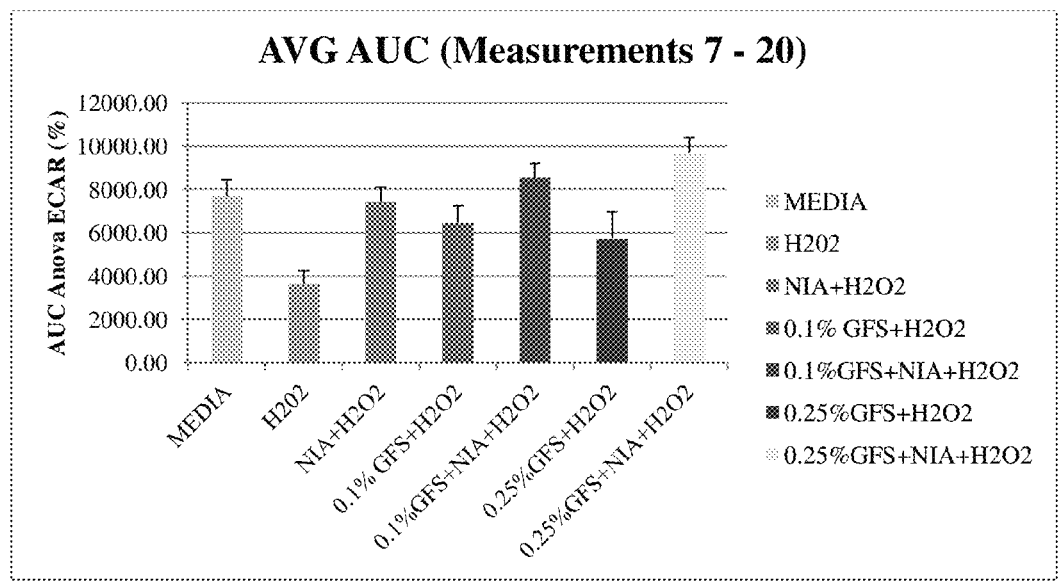
FIG. 3 shows the average area under the curve (AUC) for the ECAR as a percentage of baseline in human fibroblasts treated with hydrogen peroxide and niacinamide and/or gold silk sericin at time points 7 through 20 following treatment.

Cells were treated with 1.75 mM hydrogen peroxide and GSS at a concentration of 0.1% or 0.25% alone or in combination with 3% niacinamide. The GSS and niacinamide levels were selected to avoid cell toxicity. The ECAR was calculated as a percent of pre-treatment baseline. Control cells that were not exposed to hydrogen peroxide exhibited an ECAR above about 90% at time point 13 and above about 75% at time point 20. In contrast, cells treated with hydrogen peroxide showed a reduction in ECAR to less than about 40% at time points 13 and 20. Treatment with GSS or niacinamide provided a protective effect and increased the ECAR. Unexpectedly, treatment with a combination of GSS and niacinamide offered a greater protective effect than GSS alone and niacinamide alone, restoring the ECAR to a rate equal to or greater than in control cells (FIG. 3).

Figure 4:
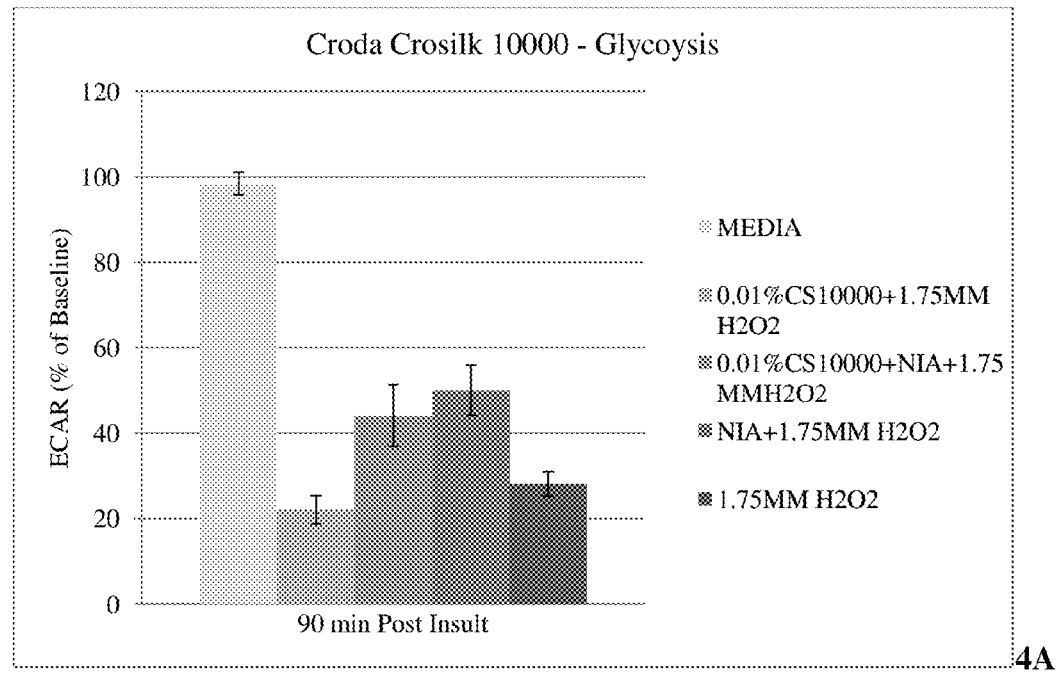
FIG. 4 shows the ECAR as a percentage of baseline in human fibroblasts treated with hydrolyzed silk protein and niacinamide at 90 minutes post-treatment.
Figure 4:
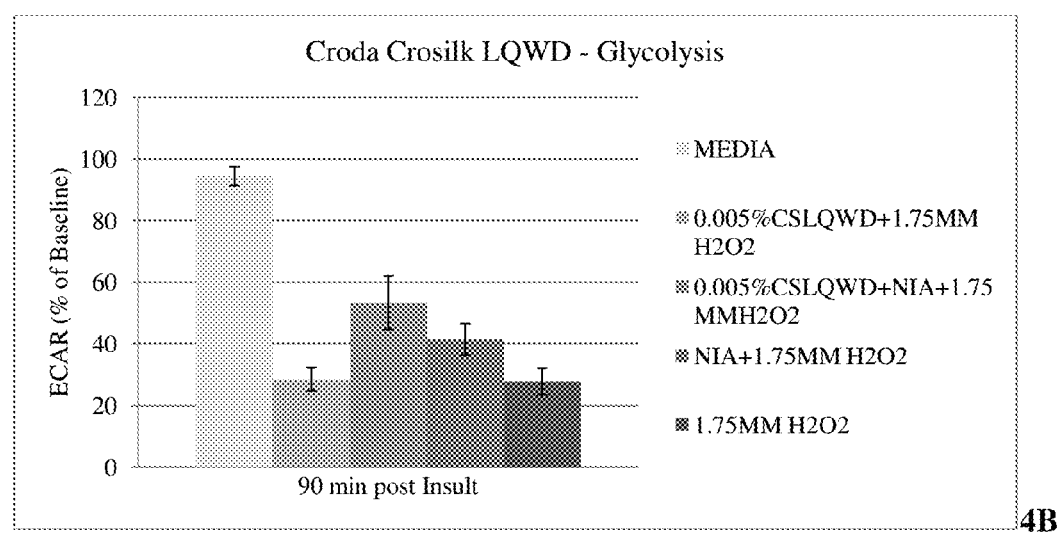
Figure 5:
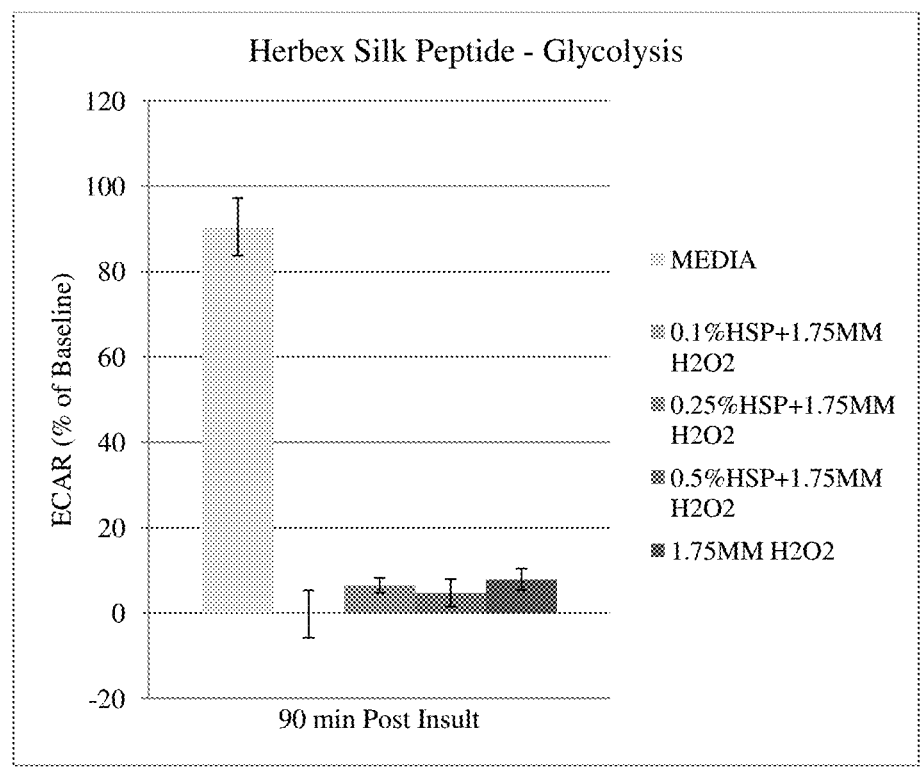
FIG. 5 shows the ECAR as a percentage of baseline in human fibroblasts treated with hydrolyzed silk sericin at various concentrations and/or hydrogen peroxide at 90 minutes post-treatment.

A comparative study was done wherein fibroblasts were treated with hydrolyzed silk protein mixtures and/or niacinamide. The hydrolyzed silk protein mixtures, Crosilk™ 10000 and Crosilk™ Liquid (Croda International) (FIG. 4) and hydrolyzed silk sericin (HerbEx Silk Peptides, BioSpectrum) did not contain flavonoids. Of the hydrolyzed silk proteins tested, only hydrolyzed silk in combination with a flavonoid compound, i.e., GSS, had a statistically significant effect on ECAR and a synergistic effect with niacinamide. The combination of either Crosilk™ compound and niacinamide was not significantly greater than treatment with the Crosilk™ compound and niacinamide alone. Additionally, while cells treated with 0.1 or 0.25% GSS exhibited a significant increase in ECAR, HerbEx Silk Peptides at concentrations of 0.1%, 0.25% or 0.5% did not provide any protective effect (FIG. 5). GSS thus provided a protective effect from a stressor-induced reduction in glycolysis that was not achieved in cells treated with hydrolyzed silk proteins without a flavonoid compound.

Example 2

The effects of a flavonoid compound, a vitamin B$_3$ compound, a hydrolyzed silk protein and a combination thereof, on intracellular ATP levels were assessed. Keratinocytes were cultured in T150 flasks in EpiLife® medium (MEPICFPRF500, Life Technologies, Grand Island, N.Y.) supplemented with human keratinocyte growth supplement (S-001-5, Life Technologies) and 1% penicillin/streptomycin (15140-122, Life Technologies). When the keratinocytes reached about 70% confluency, they were plated on 96-well plates at a density of 20,000 cells/well. The plates were incubated for 24 hours before the experimental stressor ($H_2O_2$) and treatment (niacinamide and/or GSS, Crosilk™ 1000, Crosilk™ Liquid, or HerbEx Silk Peptides) were applied.

The 96-well plate was divided into groups of wells in which (1) no stressor or treatment was applied, (2) stressor was applied but no treatment, and (3) stressor and treatment were applied. For the no stressor or treatment group, the culture medium was simply refreshed. In combination experiments, stressor and two treatments were applied. For the stressed groups, culture medium containing 500 uM $H_2O_2$ was used to replace the medium Immediately after adding the medium with $H_2O_2$, the treatments were pipetted into the wells from a 100× master stock solution in water. The plates were returned to the $CO_2$ incubator for 90 minutes before ATP was measured.

ATP was measured by removing the media from all treatment groups and controls and replacing the media with ATP Glo® reagent (Promega, Madison, Wis.) per the manufacturer's instructions. After 10 minutes of exposure at room temperature, the luminescence was measured using an EnVision® plate reader (Perkin Elmer, Waltham, Mass.). The luminescent counts that were the output from the measurement were directly proportional to the ATP levels in the cells.

Replicates of each treatment group were averaged together and standard p-value calculations were used (2-sided, equal variance) to calculate significance. In cases where two treatments appeared to synergistically enhance ATP levels, the observed results were compared to the sum of the individual treatment groups to determine significance. The ATP levels measured following treatment are provided below.

|  | ATP | % Control |
| --- | --- | --- |
| Untreated Control | 427799 | — |
| 800 uM $H_2O_2$ | 17275 | 4.0% |
| 0.05% Niacinamide + 800 uM $H_2O_2$ | 185268 | 43.3% |
| 0.025% Gold Silk Sericin + 800 uM $H_2O_2$ | 81695 | 19.1% |
| 0.1% Gold Silk Sericin + 800 uM $H_2O_2$ | 38276 | 8.9% |
| 0.025% Gold Silk Sericin + 0.05% Niacinamide + 800 uM $H_2O_2$ | 296014 | 69.2% |
| 0.1% Gold Silk Sericin + 0.05% Niacinamide + 800 uM $H_2O_2$ | 244045 | 57.0% |

Figure 6:
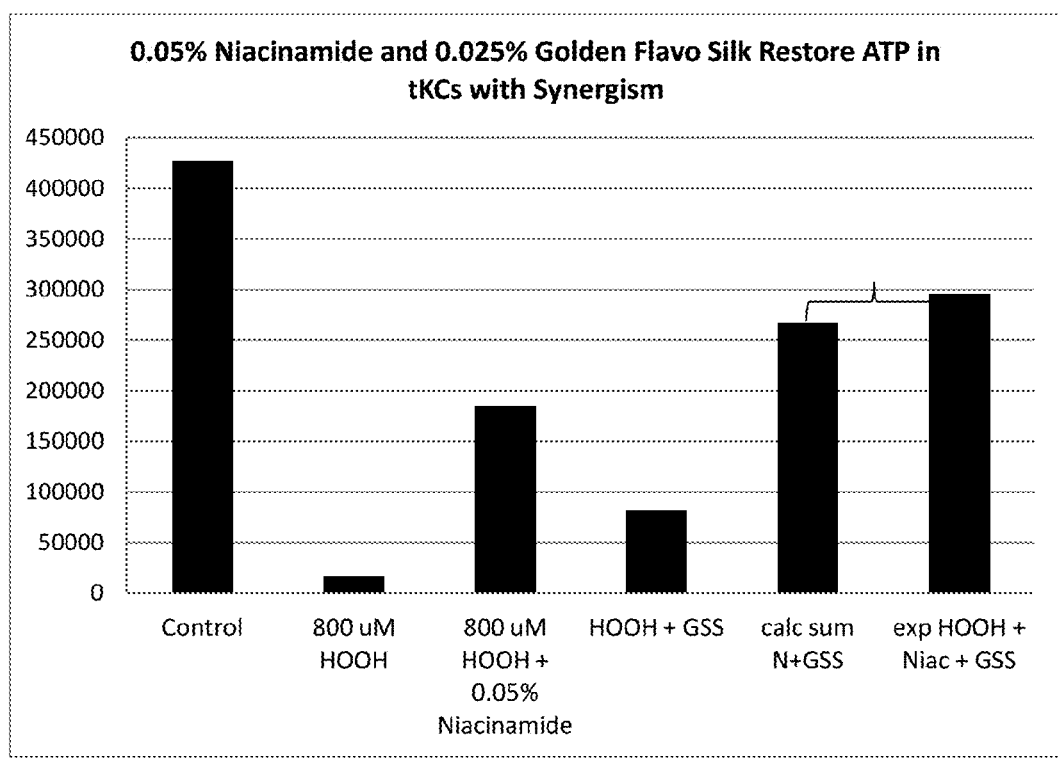
FIG. 6 shows ATP levels in human keratinocytes treated with hydrogen peroxide and niacinamide and/or gold silk sericin.

Cells treated with GSS at a concentration of 0.025% or 0.01% in combination with niacinamide had significantly higher ATP levels compared to cells treated with GSS or niacinamide alone. Cells treated with the combination of GSS with niacinamide also had ATP levels that were significantly higher than the calculated sum of the ATP levels following treatment with GSS or niacinamide alone. The sum of the ATP levels for 0.025% GSS and niacinamide was 266963, corresponding to a 15.5-fold increase in ATP levels compared to cells treated with hydrogen peroxide alone. The combination, however, produced ATP levels of 296014, corresponding to a 17.1-fold increase, which was significant (p-value=0.039; FIG. 6). Similarly, the sum of the 0.1% GSS and niacinamide was 223250, corresponding to a 12.9-fold increase in ATP levels compared to cells treated with peroxide alone; however, the combination produced ATP levels of 244045, corresponding to a 14.1-fold increase, which was significant (p-value less than 0.05).

A comparative study was done in which cells were treated with hydrolyzed silk protein mixtures (Croda Crosilk™ 10000 and Croda Crosilk™ Liquid) or hydrolyzed silk sericin (HerbEx Silk Peptides), and/or niacinamide.

|  | ATP | % Control |
| --- | --- | --- |
| Untreated Control | 290806; 275942; 283374 | — |
| 880 uM $H_2O_2$ | 8014; 7334; 7674 | 2.7% |
| 250 uM Niacinamide + 880 uM $H_2O_2$ | 85645; 75045; 80345 | 29.5% |
| 0.05% HerbEx Silk Peptides + 880 uM $H_2O_2$ | 12646 | 4.3% |
| 250 uM Niacinamide + 0.05% HerbEx Silk Peptides + 880 uM $H_2O_2$ | 95836 | 33.0% |
| 0.05% Crosilk ™ 10000 + 880 uM $H_2O_2$ | 20549 | 7.4% |
| 250 uM Niacinamide + 0.05% Crosilk ™ 10000 + 880 uM $H_2O_2$ | 186621 | 67.6% |
| 0.05% Crosilk ™ Liquid + 880 uM $H_2O_2$ | 23069 | 8.1% |
| 250 uM Niacinamide + 0.05% Crosilk ™ Liquid + 880 uM $H_2O_2$ | 118083 | 41.7% |

Measuring ATP levels at a single point in time does not provide kinetic information on the cellular processes that generate energy, i.e., glycolysis and oxidative phosphorylation, but can be combined with metabolic measurements to assess the overall protective effect of a treatment.

The foregoing Examples demonstrate that a combination of a flavonoid compound, a vitamin $B_3$ compound, and a hydrolyzed silk compound synergistically protects against cellular damage and restores ATP levels. Treatment with a combination of a flavonoid compound, a vitamin $B_3$ compound, and a hydrolyzed silk peptide, e.g., a combination of GSS and niacinamide, significantly and synergistically restored rates of glycolysis and intracellular ATP levels. Treatment with hydrolyzed silk and niacinamide alone did not confer the same protective benefits as GSS and niacinamide to stressed cells, indicating the importance of a flavonoid compound in combination treatment.

Example 3

Figure 7:
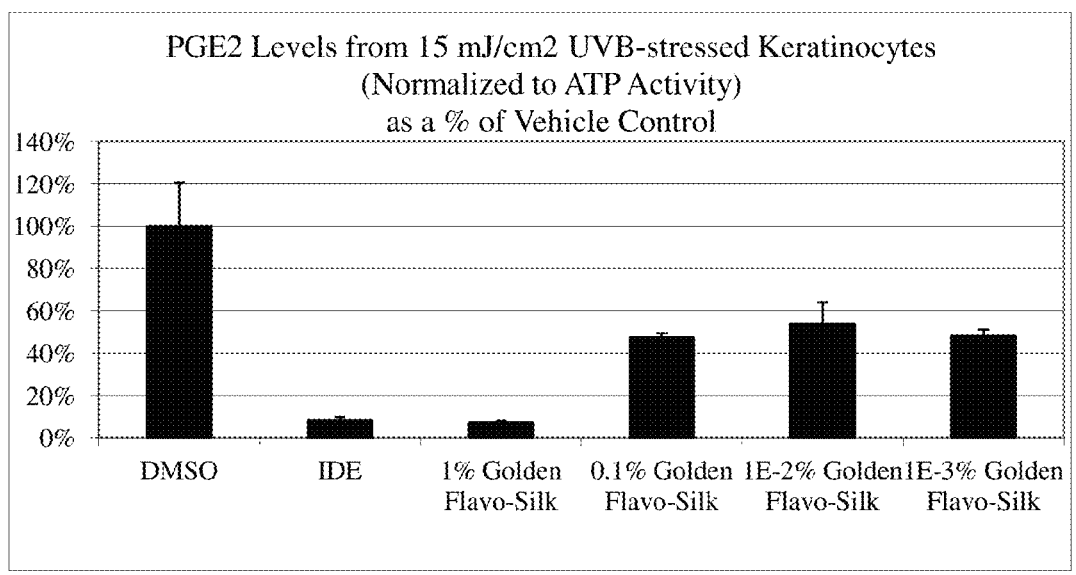
FIG. 7 shows prostaglandin E2 (PGE2) levels in human keratinocytes exposed to UV radiation and treated with various concentrations of gold silk sericin or idebenone.

The effects of GSS on inflammation were assessed using a UV stress model (FIG. 7). Human keratinocytes were exposed to 15 mJ/cm² of ultraviolet B (UVB) radiation, and prostaglandin E2 (PGE2) was quantitated after an overnight incubation. PGE2 is a lipid formed at sites of injury that is a key mediator of the inflammatory response. GSS was added to the cultures immediately after UVB exposure. Cells treated with GSS at a concentration of 0.001, 0.01, 0.1 and 1% showed a significant decrease in UVB-induced PGE2 production. GSS at a concentration of 1% blocked UVB-induced PGE2 to levels within 10% of non-UVB exposed control cells and had equal activity as the gold standard anti-inflammatory agent idebenone.

Example 4

Figure 8:
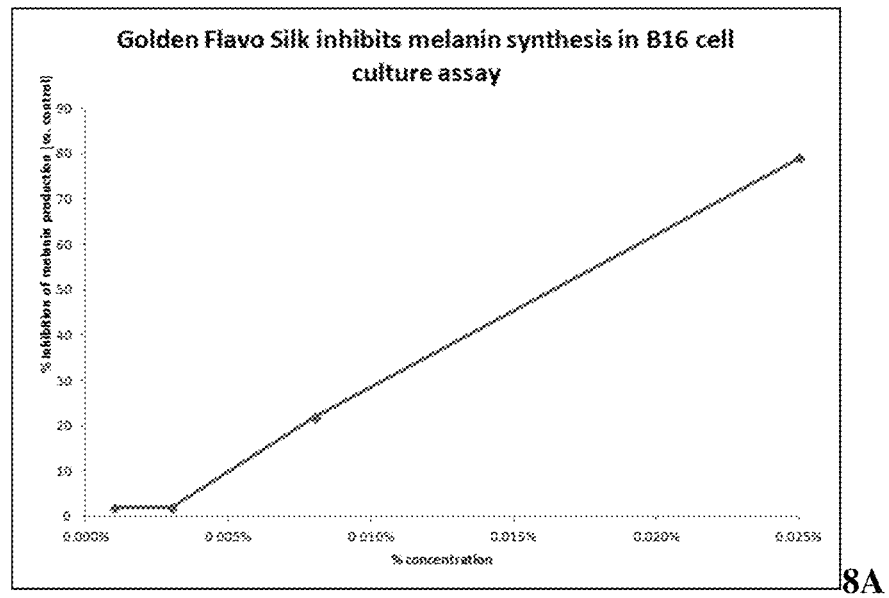
FIG. 8 shows the effect of gold silk sericin on melanogenesis.
Figure 8:
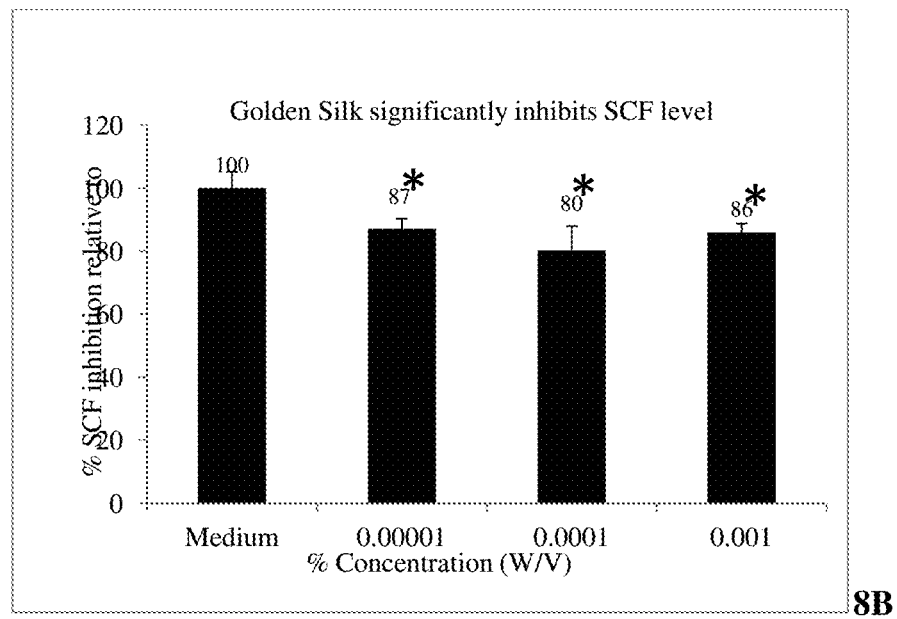

The effect of GSS on melanogenesis was assessed (FIG. 8). B16 mouse melanoma cells were treated with GSS. The melanin produced by the cells was quantified by measuring optical density at 410 nm using a UV-VIS plate reader. GSS inhibited melanin production in a dose response manner starting at 0.008% (FIG. 8A). The release of stem cell factor (SCF) protein, a melanogenic cytokine, was also assessed. Human keratinocytes were treated with GSS and the release of SCF was measured using ELISA. After three days of treatment, GSS at concentrations of 0.00001% to 0.001% significantly suppressed SCF release versus control (FIG. 8B).

Example 5

The effects of a skin care composition comprising a flavonoid compound, a vitamin $B_3$ compound, and a hydrolyzed silk protein were assessed in a clinical study. Sixty-five (65) pre-menopausal Caucasian women, aged 25-55 were enrolled in the four-week study, which was designed to measure the effects of a skin cream comprising 5 weight percent niacinamide and 2 weight percent gold silk sericin on skin hydration, tone, radiance, and firmness. The subjects used no other skin care products for the duration of the study and refrained from undergoing all other forms of skin treatment, including skin care supplements and skin care procedures. For a one-week washout period prior to the start of the study, the subjects used a standard facial cleanser and moisturizer supplied by the study sponsor.

Treatment was randomly assigned to either the right or left half of the subject's face. For the duration of the study, the subjects applied the test product twice a day to the assigned treatment side. The test product bottles were weighed after one and three weeks of treatment to test for study compliance.

Skin assessments were conducted at the start of the study (baseline), 30 minutes after the first product application, and after two and four weeks of treatment (FIG. 9). During the assessments, a photograph was taken to evaluate skin tone, fine lines, wrinkles, age spots, skin texture, and pore size. Skin hydration was measured with a Corneometer® MPA-5 (Courage+Khazaka Electronic GmbH, Germany). Skin tone was measured using a spectrophotometer (Spectrophotometer CM600d, Konica Minolta, Ramsey, N.J.). Skin firmness and elasticity was assessed using a Cutometer® (Courage+Khazaka Electronic GmbH). Additionally, the panelists answered self-assessment questions at baseline and after two and four weeks.

The subjects experienced a significant increase in skin hydration immediately following application of the test product, as well as after two and four weeks. The subjects also experienced a significant improvement in skin elasticity immediately following application of the test product, and after two and four weeks. After four weeks, the subjects experienced a significant change in skin tone. A significant number of subjects reported improvements in skin radiance, brightness, hydration, softness, plumpness, and the appearance of fine lines and wrinkles for skin treated with the test product, compared to pre-treatment and control (untreated skin).

Example 6

The effects of a skin care composition comprising a flavonoid compound, vitamin $B_3$ compound, and a hydrolyzed silk protein were assessed in a clinical study. Thirty (30) female subjects aged 40-70 were enrolled in an eight-week study. After a four-week washout period, the subjects were given a test and control product and applied each product twice daily to one-half of the face. The test product was a skin cream comprising 5 weight percent niacinamide and 2 weight percent gold silk sericin in a dermatologically acceptable vehicle. The control product was the vehicle only.

Skin assessments were conducted at the start of the study (baseline) and after four and eight weeks of treatment. During the assessments, skin surface properties were measured with a high resolution UVA-light video camera (Visioscan® VC98, Courage+Khazaka Electronic GmbH). Changes in wrinkle volume, energy, variance, roughness, and smoothness were evaluated. Skin elasticity was assessed using a Cutometer. Skin hydration was measured with a Corneometer® CM825 (Courage+Khazaka Electronic GmbH). Skin bather function was assessed used a Tewameter® TM300 (Courage+Khazaka Electronic GmbH) to measure trans-epidermal water loss (TEWL).

The skin treated with the test product comprising GSS and niacinamide exhibited significant improvements (p-value less than 0.05) in the signs of aging skin compared to skin treated with vehicle only. The test product caused significant improvement in skin surface. After four weeks, there were significant decreases in wrinkle volume (p=0.007) and overall roughness (p=0.006) and a significant increase in skin smoothness (p=0.009). After eight weeks, there was significant decreases in wrinkle volume (p=0.006), variance (p=0.002), average roughness (p=0.0001), and overall roughness (p less than 0.0001) and significant increases in energy (p=0.0003) and smoothness (p=0.02). The test product comprising GSS and niacinamide also caused significant improvements in skin elasticity. After four and eight weeks, there were significant increases in gross elasticity and net elasticity. The test product caused significant increases in skin hydration after four weeks (p=0.006) and eight weeks (p=0.0003). The test product also strengthened the barrier function of the skin, resulting in a significant decrease in TEWL after four weeks (p=0.04) and eight weeks (p less than 0.00001).

Figure 10:
FIG. 10 shows confocal microscopy images of skin treated with a skin cream comprising gold silk sericin for eight weeks.
Figure 10:
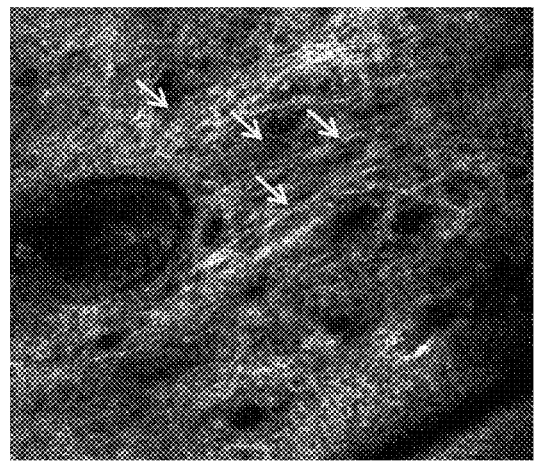
Figure 10:
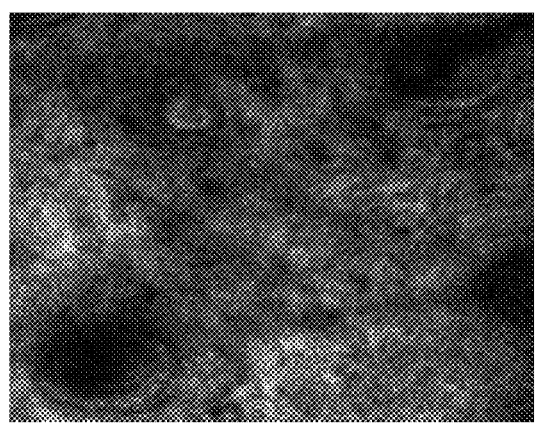

The papillary dermis was analyzed using confocal microscopy (FIG. 10). At baseline, the skin was elastotic, i.e., had degraded elastic tissue, with degenerated collagen and no fiber reflectance (FIG. 10A). After eight weeks, skin treated with the test composition comprising GSS exhibited newly formed collagen, increased reflectance, and dermal restructuring (FIG. 10B). Skin treated with the vehicle only exhibited no change from baseline (FIG. 10C).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A topical composition for effecting a visually and/or tactilely perceptible positive change or benefit in skin appearance and/or feel or delaying the appearance of aging skin, comprising:
    a safe and effective amount of gold silk sericin (GSS) comprising hydrolyzed silk sericin and flavonoid compounds;
    a safe and effective amount of niacinamide, wherein the niacinamide and gold silk sericin, in combination, synergistically increase cellular energy production; and
    a dermatologically acceptable vehicle.

2. The topical composition of claim 1, wherein the flavonoid compounds comprise a flavonol compound selected from the group consisting of quercetrin, astragalin, quercetin, kaempferol, myricitin, a glycoside of any of the foregoing and any combination thereof.

3. The topical composition of claim 1, wherein the composition comprises about 0.01 weight percent to about 5 weight percent of the hydrolyzed silk sericin and about 0.1 weight percent to about 10 weight percent of the niacinamide.

4. The topical composition of claim 1, wherein the composition comprises from about 0.00005 weight percent to about 0.005 weight percent of the flavonoid compounds and from about 0.1 weight percent to about 10 weight percent of the niacinamide.

5. The topical composition of claim 4, wherein the ratio by weight of the flavonoid compounds to the niacinamide in the composition is between about 1:10 and about 1:60.

6. A method of effecting a visually and/or tactilely perceptible positive change or benefit in skin appearance and/or feel or delaying the appearance of aging skin, comprising: applying an effective amount of a composition comprising a synergistic combination of gold silk sericin (GSS) comprising hydrolyzed silk sericin and flavonoid compounds and niacinamide and a dermatologically acceptable carrier to a skin surface, wherein the combination of niacinamide and GSS synergistically increases cellular energy production and the composition is applied for a period of time sufficient to improve the appearance of at least one sign of aging skin.

7. The method of claim 6, wherein the flavonoid compounds comprise a flavonol compound selected from the group consisting of quercetrin, astragalin, quercetin, kaempferol, myricitin, a glycoside derivative of any of the foregoing and any combination thereof.

8. The method of claim 6, wherein the composition further comprises fibroin.

9. The method of claim 6, wherein the composition comprises from about 0.01 weight percent to about 5 weight percent of the hydrolyzed silk sericin and about 0.1 weight percent to about 10 weight percent of the niacinamide.

10. The method of claim 6, wherein the composition comprises from about 0.00005 weight percent to about 0.005 weight percent of the flavonoid compounds and about 0.1 to about 10 weight percent of the niacinamide.

11. The method of claim 10, wherein the ratio by weight of the flavonoid compounds to the niacinamide in the composition is between about 1:10 and about 1:60.

* * * * *